(12) United States Patent
Cheng et al.

(10) Patent No.: US 7,825,100 B2
(45) Date of Patent: *Nov. 2, 2010

(54) SPECIFIC GRP78 EXPRESSION-INHIBITION RNAI SEQUENCE, MEDICINE THEREOF AND METHOD THEREOF

(75) Inventors: Ann-Joy Cheng, Linkou Shiang (TW); Joseph T. Chang, Linkou Shiang (TW); Ching-Chi Chiu, Daliao Shiang (TW)

(73) Assignee: Chang Gung University, Tao-Yuan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/433,264

(22) Filed: Apr. 30, 2009

(65) Prior Publication Data

US 2010/0009435 A1 Jan. 14, 2010

Related U.S. Application Data

(62) Division of application No. 12/174,997, filed on Jul. 17, 2008.

(51) Int. Cl.
*A61K 48/00* (2006.01)
*C07H 21/02* (2006.01)
*C07H 21/04* (2006.01)
*C12N 15/63* (2006.01)

(52) U.S. Cl. ...................... 514/44; 536/23.1; 536/24.5; 435/320.1

(58) Field of Classification Search ...................... None
See application file for complete search history.

(56) References Cited

U.S. PATENT DOCUMENTS 6,506,559 B1 * 1/2003 Fire et al. ...................... 435/6
2005/0118625 A1 * 6/2005 Mounts ...................... 435/6

* cited by examiner

*Primary Examiner*—Amy Bowman
(74) *Attorney, Agent, or Firm*—Muncy, Geissler, Olds, & Lowe, PLLC (57) ABSTRACT

The present invention discloses a specific GRP78 expression-inhibition RNAi sequence, a medicine thereof and a method thereof, wherein an RNAi sequence 5'-AAGGATGGTTAAT-GATGCTGAGAA-3' complementary to GRP78 forms a special hair-pin structure inside cancer cells to specifically and effectively inhibit GRP78 expression and then inhibit the canceration process, including the growth, migration, invasion, and metastasis of cancer.

3 Claims, 10 Drawing Sheets
(8 of 10 Drawing Sheet(s) Filed in Color)

Fig.1(b) NPC-BM2

Fig.1(d) OECM1

Fig.1(f) Detroit 562

Fig.1(a) NPC-BM1

Fig.1(c) NPC-076

Fig.1(e) FADU

Fig.2(a) NPC-BM 1
Fig.2(b) NPC-BM 2
Fig.2(c) NPC-076
Fig.2(d) OECM 1
Fig.2(e) FADU
Fig.2(f) Detroit 562

Fig.3 (a) NPC-BM1
Fig.3 (b) NPC-BM2
Fig.3 (c) NPC-076
Fig.3 (d) OECM1
Fig.3 (e) FADU
Fig.3 (f) Detroit 562

Fig.4(a) NPC-BM1  Fig.4(b) NPC-BM2  Fig.4(c) NPC-076

Fig.4(f) Detroit 562

Fig.4(e) FADU

Fig.4(d) OECM1

Fig.5 (a) NPC-BM1
Fig.5 (b) NPC-BM2
Fig.5 (c) NPC-076
Fig.5 (d) OECM1
Fig.5 (e) FADU
Fig.5 (f) Detroit 562

Fig.6 (a) FADU

Fig.6 (b) Detroit 562

Fig.7 (b) Detroit 562

Fig.7(a) FADU

SEQUENCE LISTING

<160> NUMBER OF SEQ ID NOS: 6

<210> SEQ ID NO 1
<211> LENGTH: 24
<212> TYPE: DNA
<213> ORGANISM: Homo sapiens

<400> SEQUENCE: 1
aaggatggtt aatgatgctg agaa                                      24

<210> SEQ ID NO 2
<211> LENGTH: 56
<212> TYPE: DNA
<213> ORGANISM: Homo sapiens

<400> SEQUENCE: 2
aaggatggtt aatgatgctg agaagaagct tgttctcagc atcattaacc atcctt    56

<210> SEQ ID NO 3
<211> LENGTH: 44
<212> TYPE: DNA
<213> ORGANISM: Homo sapiens

<400> SEQUENCE: 3
ggttaatgat gctgagaact tcgaacttct cagcatcatt aacc                44

<210> SEQ ID NO 4
<211> LENGTH: 56
<212> TYPE: DNA
<213> ORGANISM: Homo sapiens

<400> SEQUENCE: 4
aaggataatg atgctgaggg ttaagaagct tgttaaccct cagcatcatt atcctt    56

<210> SEQ ID NO 5
<211> LENGTH: 44
<212> TYPE: DNA
<213> ORGANISM: Homo sapiens

-continued

```
<400> SEQUENCE: 5
aatgatgctg agggttaact tcgaacttaa ccctcagcat catt                    44

<210> SEQ ID NO 6
<211> LENGTH: 4326
<212> TYPE: DNA
<213> ORGANISM: artificial
<220> FEATURE:
<223> OTHER INFORMATION: This is the DNA sequence of pTopo-U6 vector
      carrying GRP78-RNAi sequence, which is the sequence from 655th to
      706th base.

<400> SEQUENCE: 6
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcacccag gctttacact ttatgcttcc ggctcgtatg ttgtgtggaa     180
ttgtgagcgg ataacaattt cacacaggaa acagctatga ccatgattac gccaagctat     240
ttaggtgaca ctatagaata ctcaagctat gcatcaagct tggtaccgag ctcggatcca     300
ctagtaacgg ccgccagtgt gctggaattc gcccttgatc tgatccggcc gcatctcta     360 ggcccgcgcc ggcccctcg cacagacttg tgggagaagc tcggctactc ccctgccccg     420
gttaatttgc atataatatt tcctagtaac tatagaggct taatgtgcga taaaagacag     480
ataatctgtt cttttaata ctagctacat tttacatgat aggcttggat ttctataaga     540
gatacaaata ctaaattatt atttaaaaa acagcacaaa aggaaactca ccctaactgt     600
aaagtaattg tgtgttttga gactataaat atcccttgga gaaaagcctt gtttggatgg     660
ttaatgatgc tgagaagaag cttgttctca gcatcattaa ccatcctttt ttcacgtagt     720
ggcggccgct cgagcatgca tctagagggc ccaattcgcc ctatagtgag tcgtattaca     780
attcactggc cgtcgtttta caacgtcgtg actgggaaaa ccctggcgtt acccaactta     840
atcgccttgc agcacatccc cctttcgcca gctggcgtaa tagcgaagag gcccgcaccg     900 atcgccttc caacagttg cgcagcctga atggcgaatg gacgcgccct gtagcggcgc     960
attaagcgcg gcgggtgtgg tggttacgcg cagcgtgacc gctacacttg ccagcgccct    1020
agcgcccgct cctttcgctt tcttcccttc ctttctcgcc acgttcgccg gctttccccg    1080
tcaagctcta aatcgggggc tccctttagg gttccgattt agtgctttac ggcacctcga    1140
ccccaaaaaa cttgattagg gtgatggttc acgtagtggg ccatcgccct gatagacggt    1200
ttttcgccct ttgacgttgg agtccacgtt ctttaatagt ggactcttgt tccaaactgg    1260
aacaacactc aacccatct cggtctattc ttttgattta agggattt tgccgatttc    1320 ggcctattgg ttaaaaatg agctgattta acaaaaattt aacgcgaatt ttaacaaaat    1380
tcagggcgca agggctgcta aggaagcgg aacacgtaga aagccagtcc gcagaaacgg    1440
tgctgacccc ggatgaatgt cagctactgg gctatctgga caagggaaaa cgcaagcgca    1500
aagagaaagc aggtagcttg cagtgggctt acatggcgat agctagactg ggcggtttta    1560
tggacagcaa gcgaaccgga attgccagct ggggcgccct ctggtaaggt tgggaagccc    1620
tgcaaagtaa actggatggc tttcttgccg ccaaggatct gatggcgcag gggatcaaga    1680
tctgatcaag agacaggatg aggatcgttt cgcatgattg aacaagatgg attgcacgca    1740
ggttctccgg ccgcttgggt ggagaggcta ttcggctatg actgggcaca acagacaatc    1800
ggctgctctg atgccgccgt gttccggctg tcagcgcagg ggcgcccggt tctttttgtc    1860
aagaccgacc tgtccggtgc cctgaatgaa ctgcaggacg aggcagcgcg gctatcgtgg    1920
```

```
ctggccacga cgggcgttcc ttgcgcagct gtgctcgacg ttgtcactga agcgggaagg    1980
gactggctgc tattgggcga agtgccgggg caggatctcc tgtcatccca ccttgctcct    2040
gccgagaaag tatccatcat ggctgatgca atgcggcggc tgcatacgct tgatccggct    2100
acctgcccat tcgaccacca agcgaaacat cgcatcgagc gagcacgtac tcggatggaa    2160
gccggtcttg tcgatcagga tgatctggac gaagagcatc aggggctcgc gccagccgaa    2220
ctgttcgcca ggctcaaggc gcgcatgccc gacggcgagg atctcgtcgt gacccatggc    2280
gatgcctgct tgccgaatat catggtgaaa aatggccgct tttctggatt catcgactgt    2340
ggccggctgg gtgtggcgga ccgctatcag gacatagcgt tggctacccg tgatattgct    2400
gaagagcttg gcggcgaatg ggctgaccgc ttcctcgtgc tttacggtat cgccgctccc    2460
gattcgcagc gcatcgcctt ctatcgcctt cttgacgagt tcttctgaat gaaaaagga    2520 agagtatgag tattcaacat ttccgtgtcg cccttattcc cttttttgcg cattttgcc    2580 ttcctgtttt tgctcaccca gaaacgctgg tgaaagtaaa agatgctgaa gatcagttgg    2640
gtgcacgagt gggttacatc gaactggatc tcaacagcgg taagatcctt gagagttttc    2700
gccccgaaga acgttttcca atgatgagca cttttaaagt tctgctatgt ggcgcggtat    2760
tatcccgtat tgacgccggg caagagcaac tcggtcgccg catacactat tctcagaatg    2820
acttggttga gtactcacca gtcacagaaa agcatcttac ggatggcatg acagtaagag    2880
aattatgcag tgctgccata accatgagtg ataacactgc ggccaactta cttctgacaa    2940
cgatcggagg accgaaggag ctaaccgctt ttttgcacaa catgggggat catgtaactc    3000
gccttgatcg ttgggaaccg gagctgaatg aagccatacc aaacgacgag cgtgacacca    3060
cgatgcctgt agcaatggca acaacgttgc gcaaactatt aactggcgaa ctacttactc    3120
tagcttcccg gcaacaatta atagactgga tggaggcgga taaagttgca ggaccacttc    3180
tgcgctcggc ccttccggct ggctggttta ttgctgataa atctggagcc ggtgagcgtg    3240
ggtctcgcgg tatcattgca gcactggggc cagatggtaa gccctcccgt atcgtagtta    3300
tctacacgac ggggagtcag gcaactatgg atgaacgaaa tagacagatc gctgagatag    3360
gtgcctcact gattaagcat tggtaactgt cagaccaagt ttactcatat atactttaga    3420
ttgatttaaa acttcatttt taatttaaaa ggatctaggt gaagatcctt tttgataatc    3480
tcatgaccaa aatcccttaa cgtgagtttt cgttccactg agcgtcagac cccgtagaaa    3540
agatcaaagg atcttcttga gatccttttt ttctgcgcgt aatctgctgc ttgcaaacaa    3600
aaaaaccacc gctaccagcg gtggtttgtt tgccggatca agagctacca actctttttc    3660
cgaaggtaac tggcttcagc agagcgcaga taccaaatac tgttcttcta gtgtagccgt    3720
agttaggcca ccacttcaag aactctgtag caccgcctac atacctcgct ctgctaatcc    3780
tgttaccagt ggctgctgcc agtggcgata agtcgtgtct taccgggttg gactcaagac    3840
gatagttacc ggataaggcg cagcggtcgg gctgaacggg gggttcgtgc acacagccca    3900
gcttggagcg aacgacctac accgaactga gatacctaca gcgtgagcta tgagaaagcg    3960
ccacgcttcc cgaagggaga aaggcggaca ggtatccggt aagcggcagg gtcggaacag    4020
gagagcgcac gagggagctt ccaggggaa acgcctggta tctttatagt cctgtcgggt    4080
ttcgccacct ctgacttgag cgtcgatttt tgtgatgctc gtcaggggg cggagcctat    4140 ggaaaaacgc cagcaacgcg gcctttttac ggttcctggc cttttgctgg ccttttgctc    4200
acatgttctt tcctgcgtta tccctgatt ctgtggataa ccgtattacc gcctttgagt    4260
```

```
                                                      -continued
gagctgatac cgctcgccgc agccgaacga ccgagcgcag cgagtcagtg agcgaggaag    4320
cggaag                                                              4326
```

SPECIFIC GRP78 EXPRESSION-INHIBITION RNAI SEQUENCE, MEDICINE THEREOF AND METHOD THEREOF

CROSS REFERENCE TO RELATED APPLICATIONS

This application is a Divisional of co-pending application Ser. No. 12/174,997, filed on Jul. 17, 2008, and for which priority is claimed under 35 U.S.C. §120; and this application claims priority of Application No. 097101260 filed in Taiwan, R.O.C. on Jan. 11, 2008 under 35 U.S.C. §119; the entire contents of all of which are hereby incorporated by reference.

BACKGROUND OF THE INVENTION

1. Field of the Invention

The present invention relates to an RNA interference technology, particularly to a specific GRP78 expression-inhibition RNAi sequence, a medicine thereof and a method thereof.

2. Description of the Related Art

The 78-kDA glucose regulated protein (GRP78), also known as hsp70-5, hspA5 or Bip, is one member of the heat shock protein 70 (HSP70) family. GRP78 is a functional protein, which implements folding up a newly-synthesized protein to have an appropriate conformation in endoplasmic reticulum. According to previous researches, a crisis of cells, such as a hypoxia state or an ultraviolet radiation, will trigger GRP78 to assist in the degradation of the incorrectly folded protein. Therefore, GRP78 is thought to be a stress sensor of endoplasmic reticulum, which functions as the cyto-protection and anti-apoptosis mechanisms of cells.

It is also found in some researches that GRP78 can function as the labeled protein of breast cancer. GRP78 can help cells survive in a glucose-deficiency environment. Some researches show: a patient having overexpressed GRP78 has a higher recurrence rate no matter in what stage of cancer, and GRP78 overexpression makes cells of breast cancer have a higher chemotherapy resistance. This finding gives physicians a very important therapeutic reference. If GRP78 concentration is tested before chemotherapy, unnecessary medicine and useless therapy can be avoided. Besides, chemotherapy sensitivity can be promoted via reducing GRP78 expression.

Further, the Inventor found that GRP78 expression in head and neck cancer cells is much higher than the expression in non-cancer cells and that GRP78 expression correlates with clinical malignant indications, such as tumor size, tumor depth, lymph metastasis. Therefore, GRP78 expression can be used as a reference for tumor grading. However, in the current cancer therapeutic technology, neither molecular inhibition technology nor molecular therapeutic medicine is designed to effectively inhibit the expression of GRP78—the overexpressed gene in breast cancer/head and neck cancer.

SUMMARY OF THE INVENTION

The primary objective of the present invention is to provide a specific GRP78 expression-inhibition RNAi sequence, a medicine thereof and a method thereof, which is based on the fact that a GRP78-related RNAi sequence can effectively inhibit GRP78 expression, and whereby the growth, metastasis and invasion of cancer cells can be inhibited.

To achieve the abovementioned objective, the present invention discloses a specific GRP78 expression-inhibition RNAi sequence, a medicine thereof and a method thereof, wherein an RNA interference technology is used to inhibit GRP78 expression. In the RNA interference technology, a dicer protein recognizes a small segment of RNA having 18-24 nucleotides, which matches a messenger RNA (mRNA) inside cells, and cuts off the mRNA to inhibit the expression of a special gene. Such a method can specifically inhibit the expression of a special gene. The inhibition effect of the RNA interference technology closely correlates with the small segment of sequence, and the Inventor has found a specific sequence in GRP78, which can more effectively inhibit GRP78 expression than other sequences.

The RNA interference sequence of the present invention is 5'-AAGGATGGTTAATGATGCTGAGAA-3' (SEQ ID NO: 1), which is a sequence of 24 nucleotides beginning from Position 1821 of GRP78 mRNA and able to function as an RNA interference mechanism for GRP78 molecules inside cells. The RNA interference sequence for GRP78 can be applied to cancer-inhibition medicines. The medicine contains a plasmid carrying the RNAi sequence and can be sent into the body of a cancer patient to inhibit the growth, metastasis and invasion of cancer cells.

Below, detailed description, in cooperation with the drawings, is used to further demonstrate the objectives, characteristics and efficacies of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The specific GRP78 expression-inhibition RNAi sequence designed by the Inventor is a sequence of 24 nucleotides 5'-AAGGATGGTTAATGATGCTGAGAA-3', (SEQ ID NO: 1) which begins from Position 1821 of GRP78 mRNA. The RNAi sequence of the present invention can effectively inhibit the expression of GRP78 gene and thus can inhibit the growth of cancer cells, wherein the cancer cells include breast cancer cells and head and neck cancer cells. The theory and efficacies of the present invention will be verified with experiments on head and neck cancer cells and the analyses thereof.

The processes of the experiments are described in detailed below:

(1) Synthesizing the GRP78 expression-inhibition RNAi sequences of the present invention and the control sequences (scramble sequences), and then synthesizing the plasmids carrying the abovementioned sequences:

The GRP78-RNAi sequences are 5'-AAGGATGGTTAAT-GATGCTGAGAAgaagcttgTTCTCAG-CATCATTAACCATCCTT-3' (SEQ ID NO: 2), and
5'-GGTTAATGATGCTGAGAActtcgaacT-TCTCAGCATCATTAACC-3' (SEQ ID NO: 3).

The GRP78-scramble RNA sequences are 5'-AAG-GATAATGATGCTGAGGGTTAAgaagct-tgTTAACCCTCAGCATCATTATCCTT-3' (SEQ ID NO: 4), and 5'-AATGATGCTGAGGGTTAActtcgaacT-TAACCCTCAGCATCATT-3' (SEQ ID NO: 5).

The boldface uppercases is the restriction enzyme site cloned to the plasmid, and the lowercases is the hair-pin structure.

(2) Connecting the synthesized sequences to the expression vectors:

Two strands of the synthesized nucleotides are respectively heated to 95° C. for 10 minutes and then cooled to the ambient temperature. Thus, the synthesized sequences can match to form a two-strand GRP78-RNAi structure, wherein the GRP78-RNAi sequences are 5'-AAGGATGGTTAATGAT-GCTGAGAAgaagcttgTTCTCAGCATCATTAACCATC-CTT-3' (SEQ ID NO: 2), and 5'-GGTTAATGATGCT-GAGAActtcgaacTTCTCAGCATCATTAACC-3' (SEQ ID NO: 3), and wherein the GRP78-scramble sequences are 5'-AAGGATAATGATGCTGAGGGTTAA-gaagcttgTTAACCCTCAGCATCATTATCCTT-3' (SEQ ID NO: 4), and 5'-AATGATGCTGAGGGTTAActtcgaacT-TAACCCTCAGCATCATT-3' (SEQ ID NO: 5).

The vector is a self-manufactured pTOPO-U6 (SEQ ID NO: 6), wherein U6 promoter is cloned to a pTOPO vector. After the hair-pin structure interference sequence is formed, the EcoRV and BbsI portions of a restriction enzyme are used to dissect the expression vector, and two strands of RNAi sequences are respectively embedded into the expression vector. Next, a T4 DNA ligase is used to join them together to form a GRP78-RNAi plasmid or a GRP78-scramble plasmid. Next, the joined sequences are sent into bacteria *E. coli* and expressed therein. Then, the plasmid carrying GRP78-RNAi or GRP78-scramble is extracted.

(3) Proving that the interference sequence of the present invention is indeed able to inhibit GRP-78 expression:

With the plasmid of TOPO-U6 being the vector, one experimental group and two control groups are prepared: Control group I has a plasmid expression vector and is named the vector control group; Control group II has a recombination GRP78-RNAi sequence with none inhibition effect and is named the scramble group; the experimental group has an interference sequence plasmid and is named the GRP78-RNAi group. They are respectively transfected into head and neck cancer cell strains, such as nasopharyngeal cancer cell lines (NPC-BM1, NPC-BM2 and NPC-076), an oral cancer cell line (OECM1), laryngeal cancer cell lines (FADU and Detroit 562). After the intracellular transcript process, the GRP78-RNAi plasmid will form a special hair-pin structure inside cells.

Two days later, the cells are collected, and protein is extracted therefrom. A western blot analysis method is used to compare the GRP78 expressions in the three groups. Refer to FIGS. 1(a)-1(f). Compared with the vector control group, the interference sequence of the GRP78-RNAi group can obviously inhibit GRP78 expression. In the experiments, Actin expression is used in protein quantification, but GRP78-RNAi does not affect the expression of Actin. The GRP78-RNAi sequence of the present invention is proved to be able to specifically and effectively inhibit GRP78 expression.

Figures 1A, 1C, 1E:
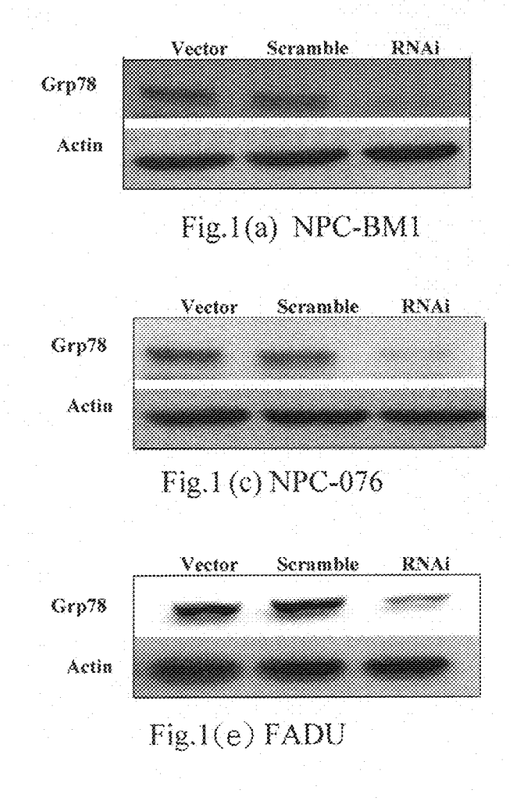
FIGS. 1(a)-1(f), 2(a)-2(f), 3(a)-3(f), 4(a)-4(f), 5(a)-5(f), 6(a)-6(b), 7(a)-7(b), 8, and 9 show experimental data according to the present invention.
Figures 1B, 1D:
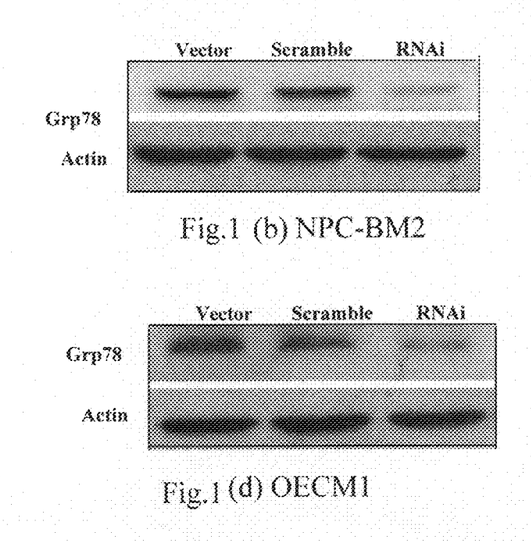
Figure 1F:
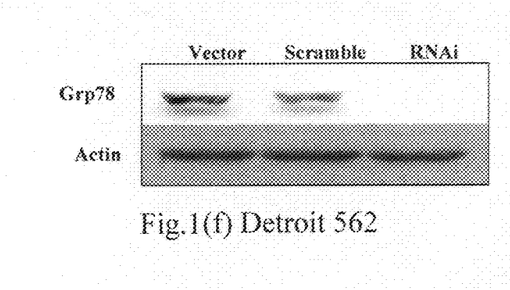
Figure 2:
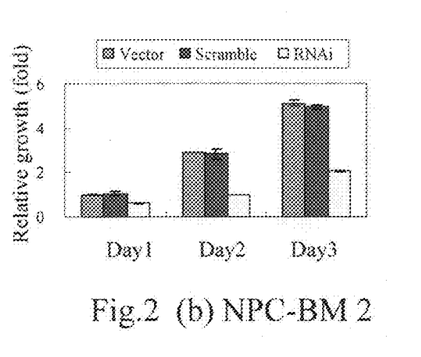
Figure 2A:
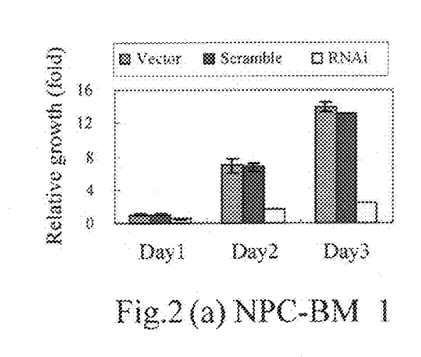
Figure 2C:
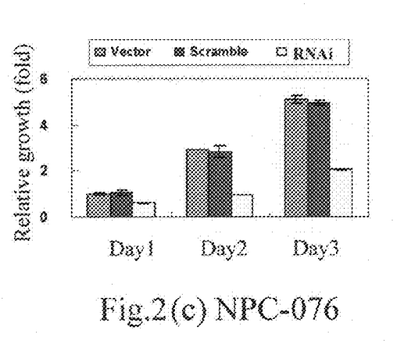
Figure 2D:
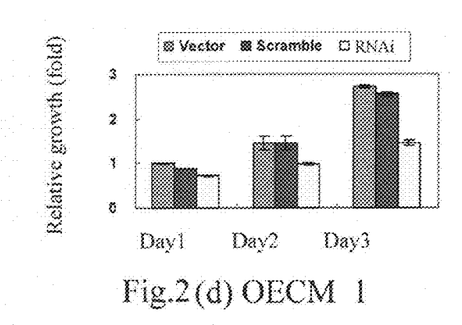
Figure 2E:
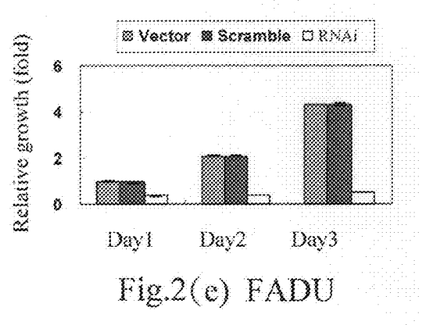
Figure 2F:
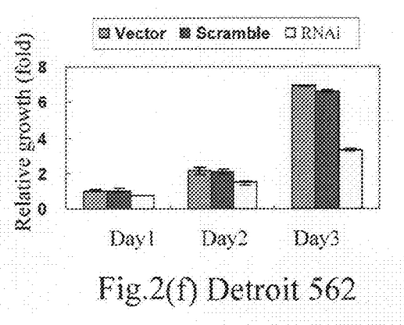
Figure 3A:
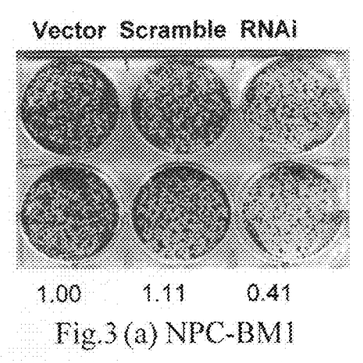
Figure 3B:
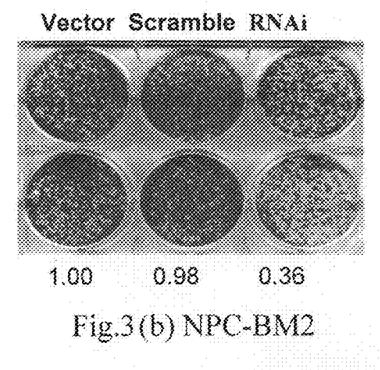
Figure 3C:
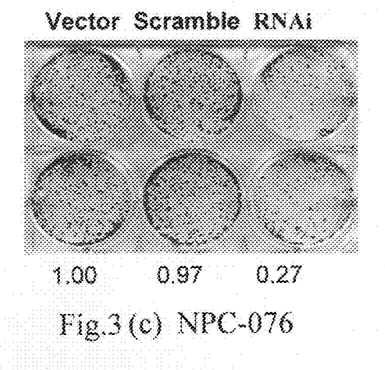
Figure 3D:
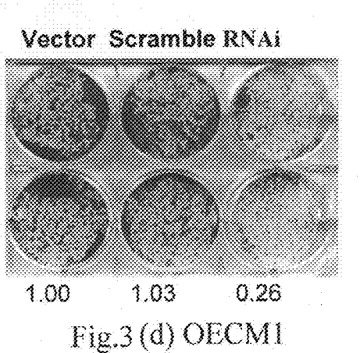
Figure 3E:
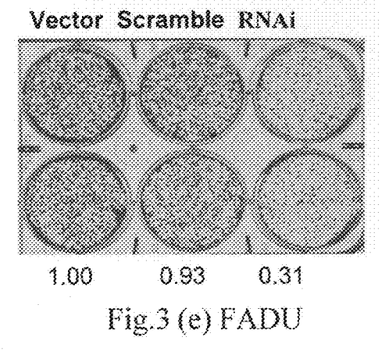
Figure 3F:
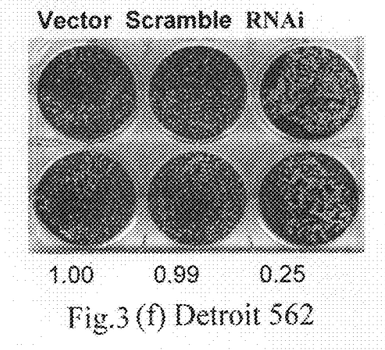
Figure 4A:
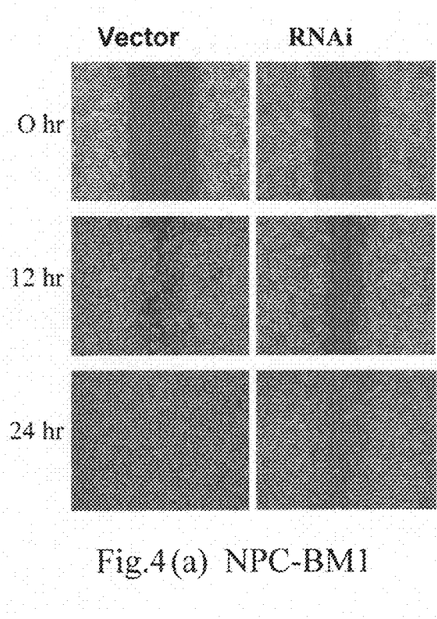
Figure 4B:
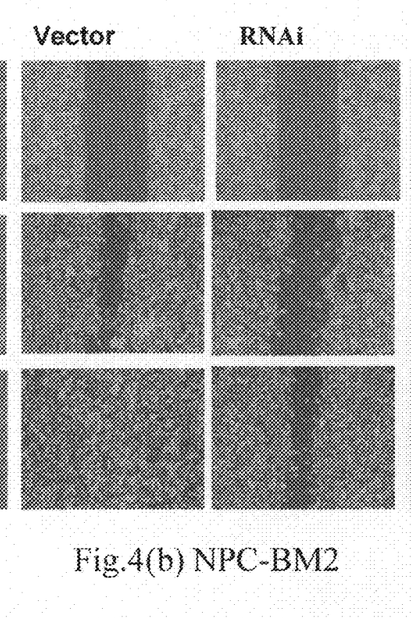
Figure 4C:
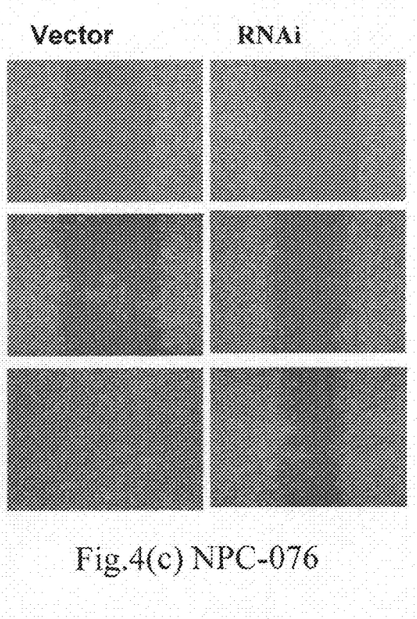
Figure 4D:
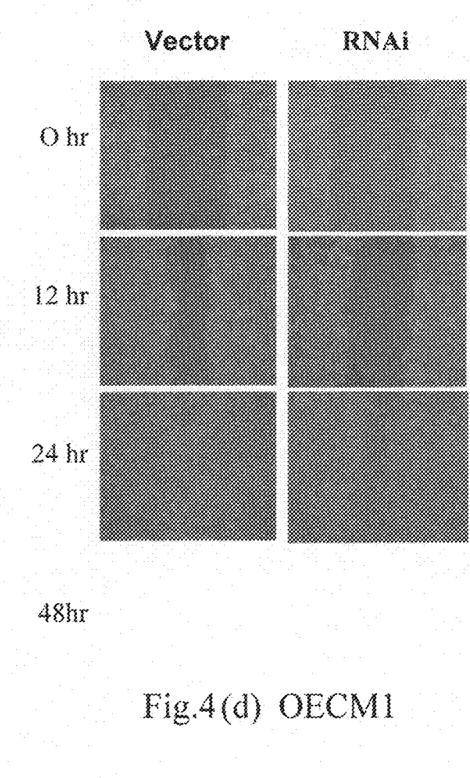
Figure 4E:
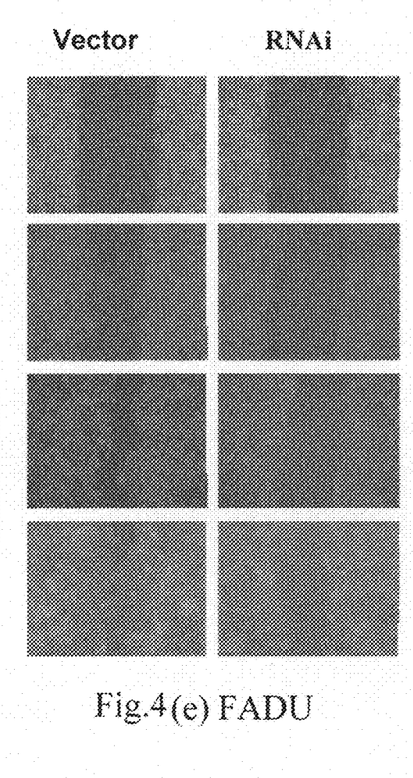
Figure 4F:
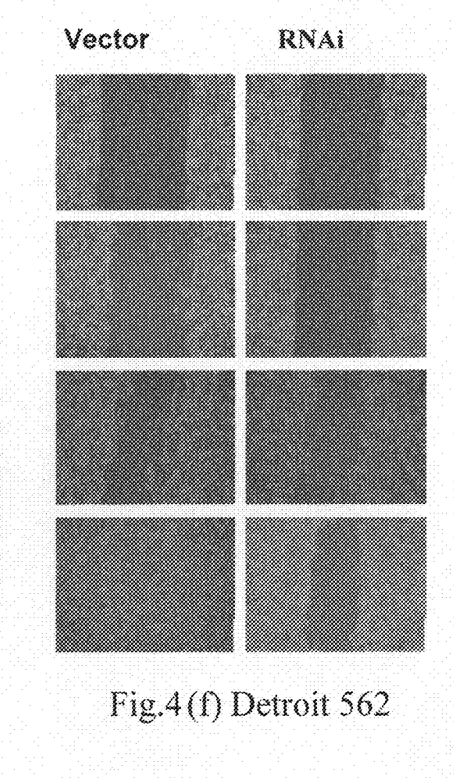
Figure 5:
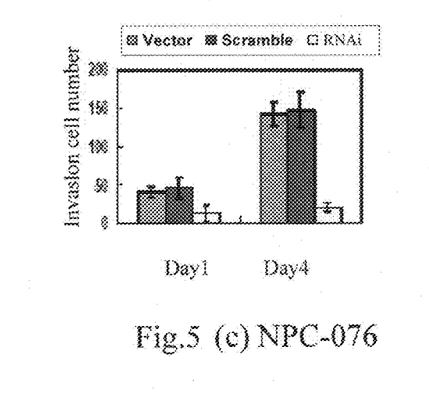
Figure 6:
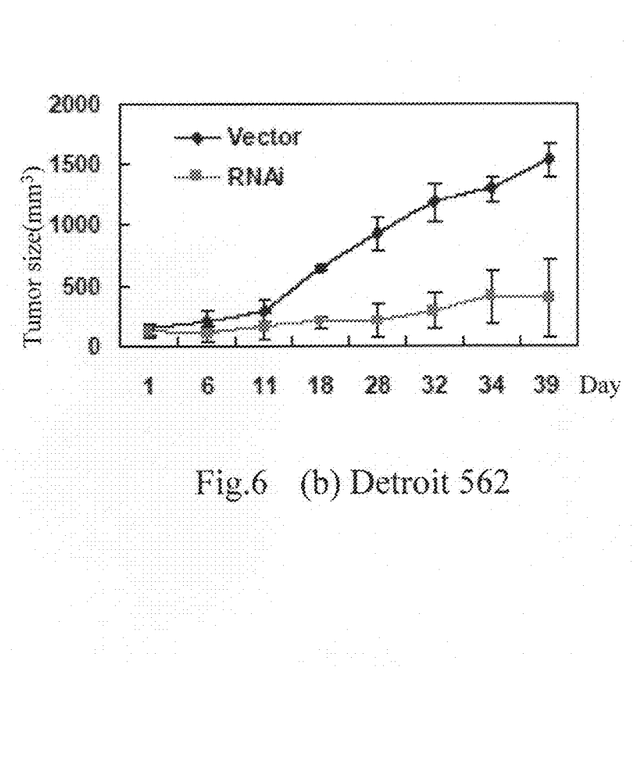
Figure 7A:
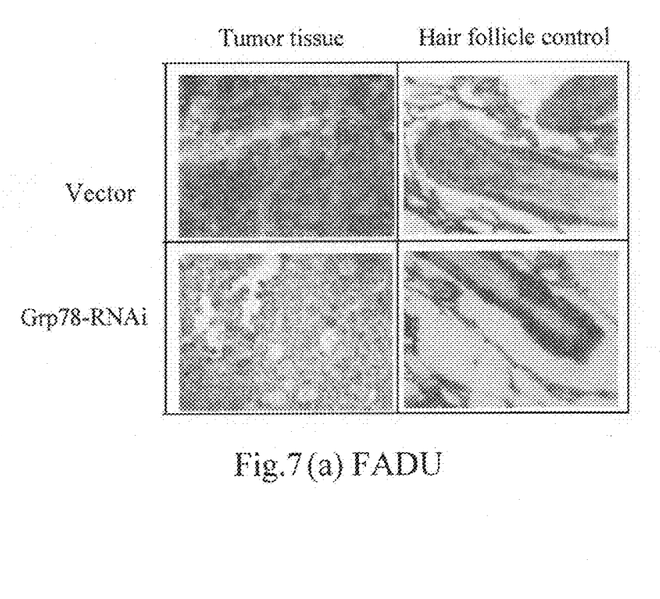
Figure 7B:
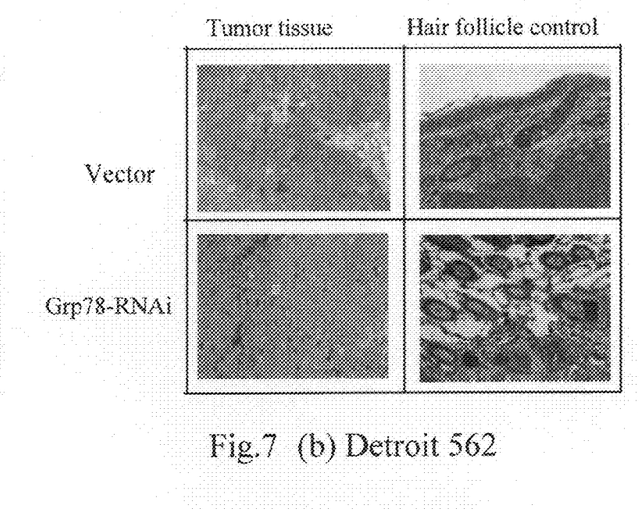
Figure 8:
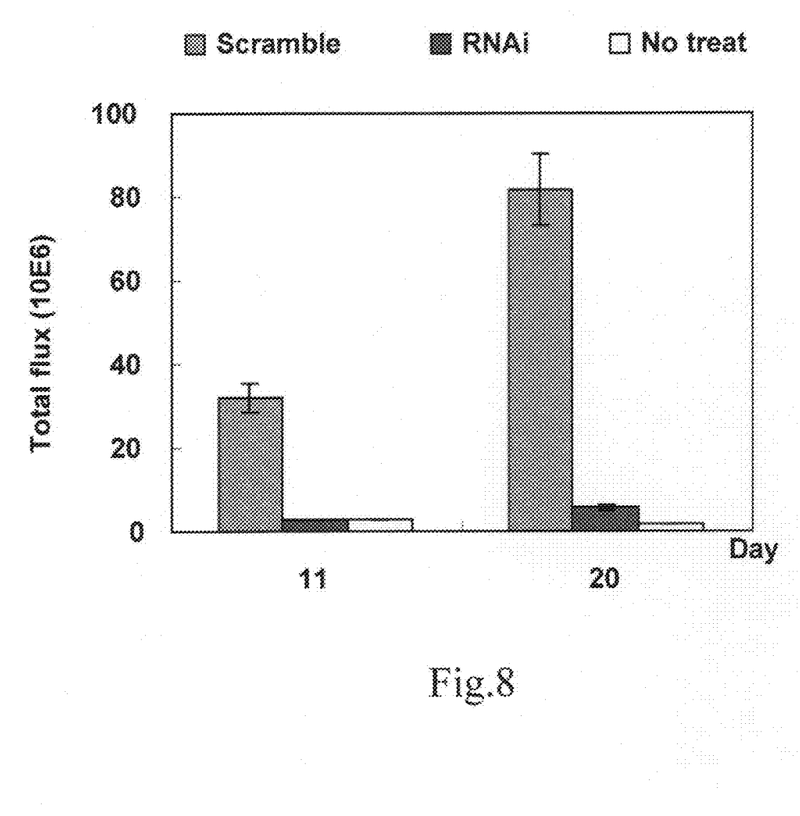

(4) Proving that the inhibition of GRP78 expression by the present invention is indeed able to inhibit the growth, metastasis and invasion of head and neck cancer cells:

a. Proving that inhibiting GRP78 expression can inhibit the growth and colony formation of head and neck cancer cells:

The expression variation of the three groups in cell facet is used to investigate the effects of the GRP78-RNAi method of the present invention. The growth of head and neck cancer cells within 1-5 days is investigated with cell count and colony formation analysis. Refer to FIGS. 2(a)-2(f). From cell count, it is shown: inhibiting GRP78 expression can inhibit the growth of cancer cells in all six cell strains. Refer to FIGS. 3(a)-3(f). Crystal violet is used to stain cells and quantify the number of cell colonies. From colony formation analysis, it is shown: the size and number of cell colony in the experimental group is smaller that that in the control groups. From the above mentioned two test methods, it is proved that the specific GRP78 expression-inhibition RNAi sequence of the present invention can indeed inhibit the growth of head and neck cancer cells.

b. Proving that inhibiting GRP78 expression can inhibit the migration and invasion of head and neck cancer cells:

In addition to the influence of the specific GRP78 expression-inhibition RNAi sequence on the growth of head and neck cancer cells, the influence thereof on the migration and invasion of cancer cells is also investigated herein. A wound healing assay is used to investigate the influence of the GRP78 expression-inhibition RNAi sequence on the mobility of head and neck cancer cells. Head and neck cancer cells are planted on the bottom of culture dishes, and a sharpened plastic tip is used to generate artificial wounds. Refer to FIGS. 4(a)-4(f). From analyzing the healing capability of the artificial wounds and the cell mobility, it is proved that inhibiting GRP78 expression can inhibit the mobility of head and neck cancer cells. A Transwell invasion assay is used to investigate the invasion capability of cancer cells, wherein on the upper layer of the Transwell has a layer of Matrigel. If the cancer cells are aggressive invasion, they will digest Matrigel and invade from the upper chamber of Transwell to the lower chamber. From FIGS. 5(a)-5(f), it is proved that the specific GRP78 expression-inhibition RNAi sequence can indeed inhibit the invasion of head and neck cancer cells.

c. Proving with an in vivo method that inhibiting GRP78 expression can inhibit the growth of cancer cells:

Five-week-old BALB/C nude mice are used in the in vivo experiment. Total of $10^7$ of FADU and Detroit 562 laryngeal cancer cells are subcutaneously implanted in the nude mice. Three days later, 50 μg of the control-group vectors or 50 μg of the GRP78-RNAi plasmid (vectors carrying the GRP78-RNAi sequence) are respectively injected into the nude mice from the caudal veins thereof. Then, two doses of 25 μg GRP78-RNAi plasmid or vectors are further injected into the nude mice each week. Each group has eight mice, and the duration of the experiments is eight weeks. The lengths, widths and heights of cancers are measured to calculate the volumes of cancers and monitor the growth states of cancers. Refer to FIGS. 6(a)-6(b). In the experimental group, GRP78 expression is inhibited, and the xenografted cancer cells grow slowly. In the control groups, cancer cells grow persistently. In the experiment of FADU cancer cells, the cancer is 44% inhibited (P=0.003) in the eighteenth day, and 69% inhibited (P=0.004) in the thirty-fourth day. In the experiment of Detroit cancer cells, the cancer is 60% inhibited (P=0.017) in the eighteenth day, and 66% inhibited (P=0.016) in the thirty-ninth day. Six weeks later, the cancer tissues are taken off from the nude mice, and an immunohistochemistry method is used to analyze GRP78 expression in cancer tissues. Refer to FIGS. 7(a)-7(b). It is proved from the test on the cancer sections that GRP78 expression is inhibited by the RANi sequence of the present invention. The experiment proves that inhibiting GRP78 expression can indeed inhibit the growth of in vivo cancer cells.

d. Proving with an in vivo method that inhibiting GRP78 expression can inhibit the metastasis of cancer cells:

The IVIS system (In vivo imaging system) was used to monitor metastatic potential using Fadu xenograft mice model. First, the Fadu cell line stably transfected with luciferase gene was established. The Fadu cells were injected with 5×105 cells through the tail vein. Three days after tumor cell xenografting, the mice were randomly divided into 3 groups of 7 mice each. The experimental group was injected intravenously with 50 µl of Grp78-RNAi plasmid in 50 µl PBS, followed by a booster of 25 µg of the plasmid in 25 µl PBS twice a week for 3 weeks. The two control groups were injected on the same schedule as the experimental group but with either vector or scramble plasmids. For IVIS examination, luciferin substrate (100 µl of 30 mg/ml in PBS) was injected subcutaneously. After 10 min, mice were anesthetized with an isoflurane-oxygen mixture. Photoemissions from the luciferin-luciferase reaction were detected with a sensitive CCD camera. The imaging system first produced a photographic image in the chamber under dim illumination, followed by luminescent image acquisition. The overlay of the pseudocolor images represents the spatial distribution of photo counts produced by active luciferase. Living Image software (Xenogen) was used to integrate the bioluminescence signals and measure photo flux obtained from the mice. Refer to FIG. 8. The lucerin flux in the group of RNAi treated mice was significantly lower than in scramble-plasmid treated controls. Quantitation for the lucerin flux showed average reductions to 8.8% at day 11 and 7.0% at day 20.

Figure 9:
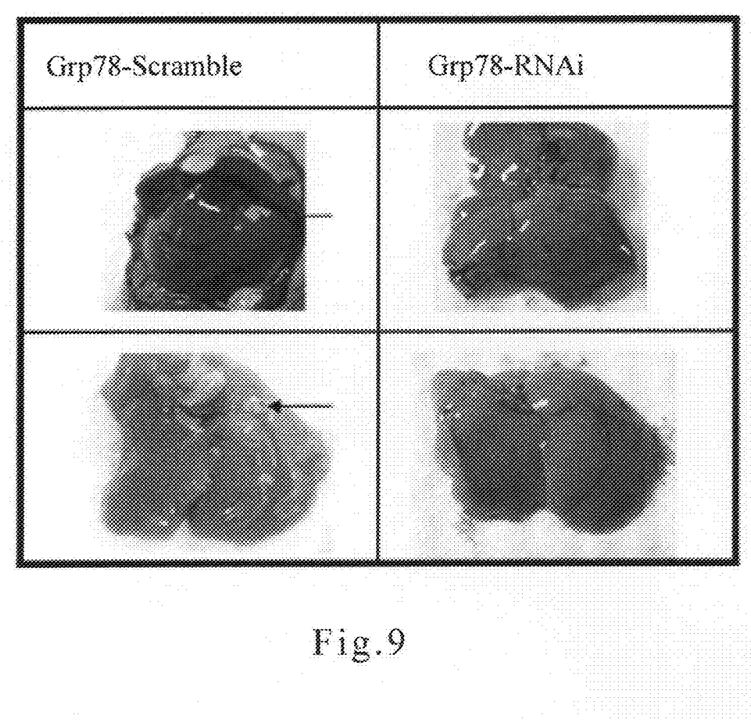

The mice were then sacrificed and the livers were examined to evaluate the metastatic potential of the tumor xenografts. Refer to FIG. 9. Examination on the livers of the RNAi treated mice also demonstrated that Grp78 knockdown suppressed tumor metastasized to the organs. Six of the 7 mice in scramble-treated groups had one or more liver tumor mass, whereas none of tumor was found in the livers of RNAi treated group.

In conclusion, the present invention discloses a specific GRP78 expression-inhibition RNAi sequence, a medicine thereof and a method thereof, wherein an RNA interference technology is used to specifically and effectively inhibit intracellular GRP78 expression and then inhibit the canceration process, including the growth, migration, invasion and metastasis of cancer. The present invention can specifically suppress GRP78 expression in the high level of cancer cells, thus, reduce damage of non-cancer cells and decrease the side-effect of chemotherapy.

The embodiments described above are only to exemplify the present invention but not to limit the scope of the present invention. Any equivalent modification or variation according to the spirit of the present invention is to be also included within the scope of the present invention, which is based on the claims stated below.

What is claimed is:

1. A medicine for specifically inhibiting 78-kDA glucose regulated protein (GRP78) expression, which contains a plasmid carrying an RNA interference (RNAi) sequence and is used to inhibit growth, migration, invasion, and metastasis of cancer cells, wherein said RNA interference sequence is 5'-AAGGATGGTTAATGATGCTGAGAA-3' and the complement thereof.

2. The medicine for specifically inhibiting 78-kDA glucose regulated protein expression of claim 1, wherein said cancer cells are head and neck cancer cells.

3. The medicine for specifically inhibiting 78-kDA glucose regulated protein expression of claim 2, wherein said head and neck cancer cells include laryngeal cancer cells.

* * * * *